United States Patent
Takami

(10) Patent No.: US 10,206,734 B2
(45) Date of Patent: Feb. 19, 2019

(54) HIGH-FREQUENCY GENERATOR FOR ELECTRIC SURGICAL INSTRUMENT

(71) Applicant: OLYMPUS CORPORATION, Hachioji-shi, Tokyo (JP)

(72) Inventor: Sadayoshi Takami, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/704,442

(22) Filed: Sep. 14, 2017

(65) Prior Publication Data
US 2018/0042663 A1 Feb. 15, 2018

Related U.S. Application Data

(63) Continuation of application No. PCT/JP2016/073608, filed on Aug. 10, 2016.

(51) Int. Cl.
*A61B 18/12* (2006.01)
*H03H 7/01* (2006.01)
*H03H 11/04* (2006.01)
*A61B 17/00* (2006.01)
(Continued)

(52) U.S. Cl.
CPC ...... *A61B 18/1233* (2013.01); *A61B 18/1206* (2013.01); *H03H 7/0115* (2013.01); *H03H 11/04* (2013.01); *A61B 2017/00734* (2013.01); *A61B 2017/00973* (2013.01); *A61B 2018/00178* (2013.01); *H02M 7/537* (2013.01)

(58) Field of Classification Search
CPC ...... A61B 18/1233; A61B 2017/00734; A61B 2017/00973; A61B 2018/00178; H02M 7/537; H03H 11/04; H03H 7/0115
See application file for complete search history.

(56) References Cited

U.S. PATENT DOCUMENTS

| 4,116,198 A * | 9/1978 | Roos ...................... A61B 18/12 606/46 |
| 2007/0118102 A1* | 5/2007 | Mihori ............... A61B 18/1206 606/32 |

(Continued)

FOREIGN PATENT DOCUMENTS

| JP | H10-118094 A | 5/1998 |
| JP | 2002-537938 A | 11/2002 |

(Continued)

OTHER PUBLICATIONS

Oct. 25, 2016 Written Opinion issued in International Patent Application No. PCT/JP2016/073608.

(Continued)

*Primary Examiner* — Daniel Fowler
(74) *Attorney, Agent, or Firm* — Oliff PLC

(57) ABSTRACT

A high-frequency generator for an electric surgical instrument that treats a living tissue includes a power supply that generates a power, and a resonant circuit that excites a high-frequency signal. The resonant circuit includes a parallel resonant circuit which is connected to the power supply, and a series resonant circuit which is coupled to the parallel resonant circuit and is connected to the electric surgical instrument. The parallel resonant circuit has a higher parallel resonant frequency than a series resonant frequency of the series resonant circuit.

7 Claims, 4 Drawing Sheets

(51) Int. Cl.
    *A61B 18/00*     (2006.01)
    *H02M 7/537*    (2006.01)

(56) References Cited

U.S. PATENT DOCUMENTS

| | | | |
|---|---|---|---|
| 2007/0225698 A1* | 9/2007 | Orszulak | A61B 18/1206 606/34 |
| 2010/0198213 A1* | 8/2010 | Lario Garcia | A61B 18/1206 606/33 |
| 2011/0160718 A1* | 6/2011 | Werner | A61B 18/12 606/39 |
| 2011/0170321 A1* | 7/2011 | Schall | A61B 18/1206 363/37 |
| 2011/0172656 A1 | 7/2011 | Schall et al. | |

FOREIGN PATENT DOCUMENTS

| | | |
|---|---|---|
| JP | 2011-067590 A | 4/2011 |
| JP | 2012-500678 A | 1/2012 |
| WO | 2010/025815 A1 | 3/2010 |
| WO | 2010/025818 A1 | 3/2010 |
| WO | 2018/029824 A1 | 2/2018 |

OTHER PUBLICATIONS

Oct. 25, 2016 Search Report issued in International Patent Application No. PCT/JP2016/073608.

Dec. 19, 2018 Search Report issued in European Patent Application No. 16893798.5.

\* cited by examiner

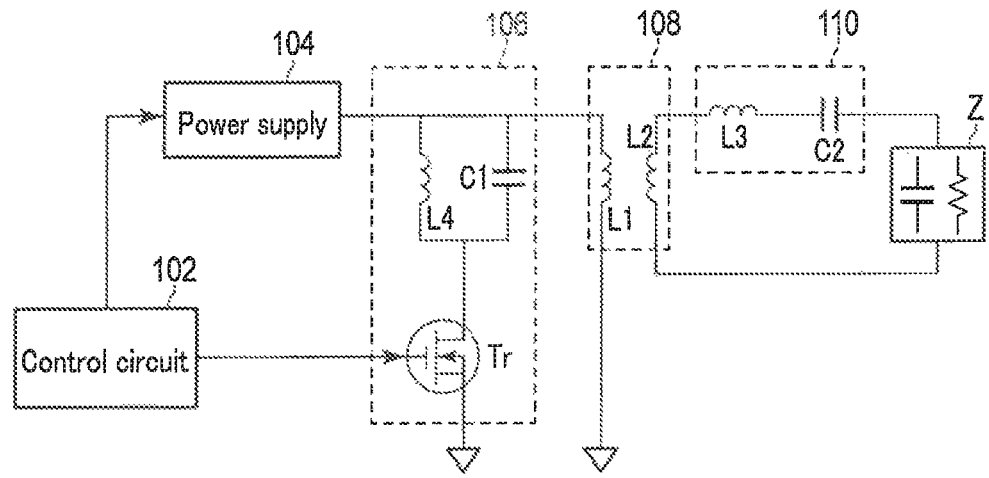
F I G. 4
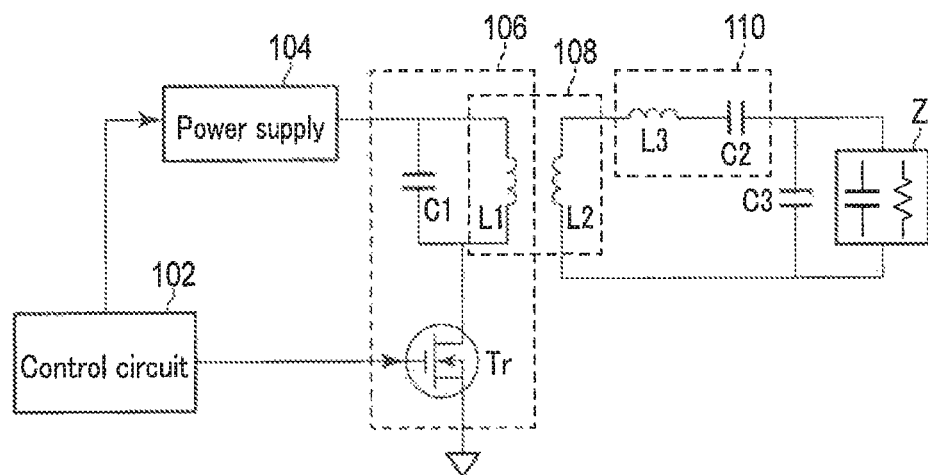
F I G. 5

HIGH-FREQUENCY GENERATOR FOR ELECTRIC SURGICAL INSTRUMENT

CROSS-REFERENCE TO RELATED APPLICATIONS

This application is a Continuation Application of PCT Application No. PCT/JP2016/073608, filed Aug. 10, 2016, the entire contents of which are incorporated herein by reference.

BACKGROUND OF THE INVENTION

1. Field of the Invention

The present invention relates to a high-frequency generator for an electric surgical instrument.

2. Description of the Related Art

As a high-frequency generator for an electric surgical instrument such as an electric scalpel, which treats a living tissue using a high-frequency signal, there exists a high-frequency generator proposed in, for example, International Publication No. 2010/025818. The high-frequency generator proposed in International Publication No. 2010/025818 includes a power supply, a parallel resonant circuit connected to the power supply, and a series resonant circuit coupled to the parallel resonant circuit through a transformer.

BRIEF SUMMARY OF THE INVENTION

A high-frequency generator according to an aspect of the invention is a high-frequency generator for an electric surgical instrument that treats a living tissue, the high-frequency generator comprising: a power supply that generates a power; and a resonant circuit that includes a parallel resonant circuit and a series resonant circuit, and excites a high-frequency signal based on the power, the parallel resonant circuit being connected to the power supply, the series resonant circuit being coupled to the parallel resonant circuit and being connected to the electric surgical instrument, wherein the parallel resonant circuit has a higher parallel resonant frequency than a series resonant frequency of the series resonant circuit.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 4 is a view showing a configuration of a power supply device according to the first modification.

FIG. 5 is a view showing a configuration of a power supply device according to the second modification.

DETAILED DESCRIPTION OF THE INVENTION

Figure 1:
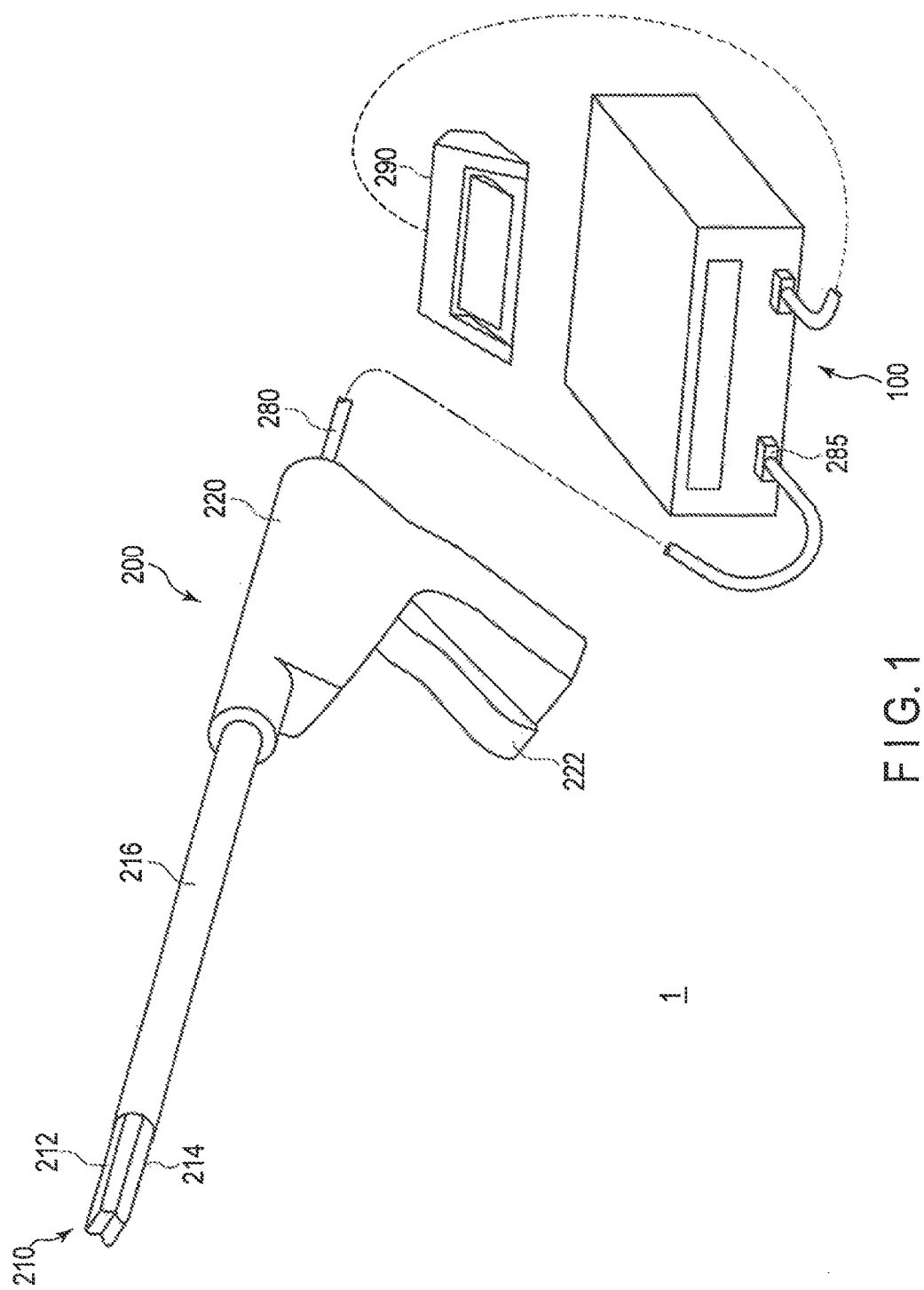
FIG. 1 is a schematic diagram of an exterior of a surgical system including a power supply device as a high-frequency generator according to one embodiment of the present invention.

Hereinafter, embodiments of the present invention will be described with reference to the drawings. FIG. 1 is a schematic diagram of an exterior of a surgical system 1 including a power supply device as a high-frequency generator according to the present embodiment. The surgical system 1 is used for treatment of a living tissue. This treatment includes, for example, hemostasis and solidification, sealing, separation, incision of a tissue. The surgical system 1 performs such treatment by applying a high-frequency current to a living tissue.

As shown in FIG. 1, the surgical system 1 includes a power supply device 100 and an electric surgical instrument 200. The electric surgical instrument 200 is a surgical instrument for surgery treatment, which is used to perform treatment by penetrating the abdominal wall, for example. The electric surgical instrument 200 includes a body 220, a shaft 216, and a distal end portion 210. The electric surgical instrument 200 described hereinafter is one example and is modifiable as appropriate. Various modifications may be made, for example, to a shape of the body 220, a shape of the shaft 216, a presence or absence of an operation knob 222, and a shape of the distal end portion 210. The electric surgical instrument 200 is not limited to that configured to treat the inside of the abdominal cavity. For example, the electric surgical instrument 200 may be configured to treat the inside of a joint cavity.

The distal end portion 210 as one example includes the first holding member 212 and the second holding member 214. This distal end portion 210 is configured to hold a living tissue between the first holding member 212 and the second holding member 214. The first holding member 212 and the second holding member 214 include surfaces, respectively, which are brought in contact with a living tissue and are provided with electrodes, respectively. A high-frequency signal is applied between these electrodes. This application of a high-frequency signal is accompanied by flow of a high-frequency current into a living tissue held between the electrodes. This flow causes the living tissue to generate heat. The living tissue is treated in this manner.

The shaft 216 projects from the body 220 and defines the longitudinal axis direction. This shaft 216 is provided with the distal end portion 210 (the first holding member 212 and the second holding member 214) on its distal end side. The shaft 216 is internally provided with, for example, a wire to transmit a force for displacing the first holding member 212 with respect to the second holding member 214. This wire displaces at least one of the first holding member 212 and the second holding member 214 in linkage with operation of the operation knob 222 of the body 220. The shaft 216 is internally provided with signal lines connected to the electrodes of the first holding member 212 and the second holding member 214, respectively. These signal lines are connected to the power supply device 100.

In the electric surgical instrument 200, the body 220 is a part to be held by an operator. The operation knob 222 for operating the distal end portion 210 is attached to the body 220. For example, the distal end portion 210 is opened and closed by an operator operating the operation knob 222.

The power supply device 100 is connected to the electric surgical instrument 200 through a cable 280. The power supply device 100 excites a high-frequency signal based on a power generated by a power source and applies this high-frequency signal to the electrodes of the first holding member 212 and the second holding member 214 through signal lines provided inside the cable 280. The cable 280 and the power supply device 100 are detachably attachable to each other through a cable connector 285. With such a configuration, the electric surgical instrument 200 is replaceable with respect to the power supply device 100.

A foot switch 290 is connected to the power supply device 100. The foot switch 290 is operated by an operator to switch ON/OFF of a high-frequency signal applied from the power supply device 100 to the electric surgical instrument 200. FIG. 1 shows an example in which ON/OFF of a high-frequency signal applied from the power supply device 100 to the electric surgical instrument 200 is switched by means of the foot switch 290. The foot switch 290 may be replaced with a hand switch to be operated with a hand, or any other switch. Such a hand switch or the like may be provided in the body 220 of the electric surgical instrument 200.

Figure 2:
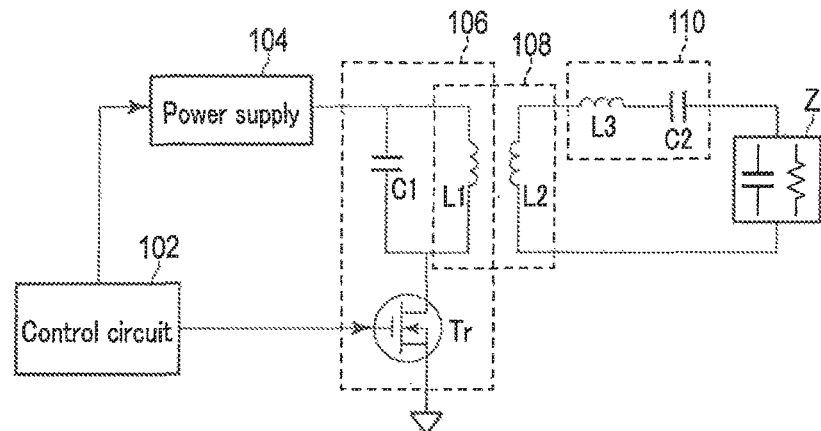
FIG. 2 is a view showing a configuration of the power supply device as one example.

Next, the power supply device 100 as a high-frequency generator according to the present embodiment will be further described. FIG. 2 is a view showing a configuration of the power supply device 100 as one example. As shown in FIG. 2, the power supply device 100 includes a control circuit 102, a power source 104, a parallel resonant circuit 106, a transformer 108, and a series resonant circuit 110.

The control circuit 102 includes, for example, a CPU and an ASIC, and switches ON/OFF of operation of the power supply 104 as well as values of a power generated at the power source 104 in response to operation of the foot switch 290. The control circuit 102 controls a switch Tr of the series resonant circuit 110.

The power supply 104 is configured to generate a DC power, for example. The power supply 104 generates a DC power by converting an AC power supplied from a commercial power supply, for example. The power supply 104 may be a rechargeable secondary battery power supply.

The parallel resonant circuit 106 includes a condenser C1 and a coil L1 with their one ends connected in parallel with respect to the power source 104. The parallel resonant circuit 106 further includes the switch Tr connected to the other ends of the condenser C1 and the coil L1. The switch Tr is, for example, an MOSFET switch. The switch Tr has a gate connected to the control circuit 102. The switch Tr has a drain connected to the other ends of the condenser C1 and the coil L1. The switch Tr has a source grounded. The parallel resonant circuit 106 configured as described above charges and discharges a power of the power supply 104 in accordance with ON/OFF of the switch Tr. The ON/OFF frequency of the switch Tr corresponds to the frequency of the electric surgical instrument 200. The parallel resonant circuit 106, therefore, functions as a circuit which excites a high-frequency signal from a power generated at the power supply 104.

The transformer 108 includes the coil L1 forming a primary winding, and a coil L2 forming a secondary winding. That is, the coil L1 is shared by the parallel resonant circuit 106 and the transformer 108. This transformer 108 transforms a voltage of a high-frequency signal excited at the parallel resonant circuit 106.

The series resonant circuit 110 includes a coil L3 and a condenser C2 with their one ends connected in series with respect to the coil L2 as the secondary winding. That is, the coil L3 as an input terminal of the series resonant circuit 110 has one end connected to the coil L2. The condenser C2 has one end connected to the other end of the coil L3. The condenser C2 as an output terminal of the series resonant circuit 110 is connected to an electrode provided in the distal end portion 210 of the electric surgical instrument 200, through a signal line provided in the shaft 216. At the time of treatment, this electrode is brought in contact with a living tissue as a load Z. This series resonant circuit 110 functions as a bandpass filter which allows passage of a signal in a specific bandwidth (a bandwidth including at least a driving frequency of the electric surgical instrument 200) of input high-frequency signals. The high-frequency signal input at the series resonant circuit 110 is converted into a sinusoidal signal at the series resonant circuit 110 and is then applied to the electric surgical instrument 200.

In this embodiment, inductance values of the coils L1 and L3 and capacitance values of the condensers C1 and C2 are set in a manner that a parallel resonant frequency of the parallel resonant circuit 106 has a higher value than that of a series resonant frequency of the series resonant circuit 110. This is to maximize the efficiency when a living tissue becomes a high load. The detailed explanations will follow.

Figure 3:
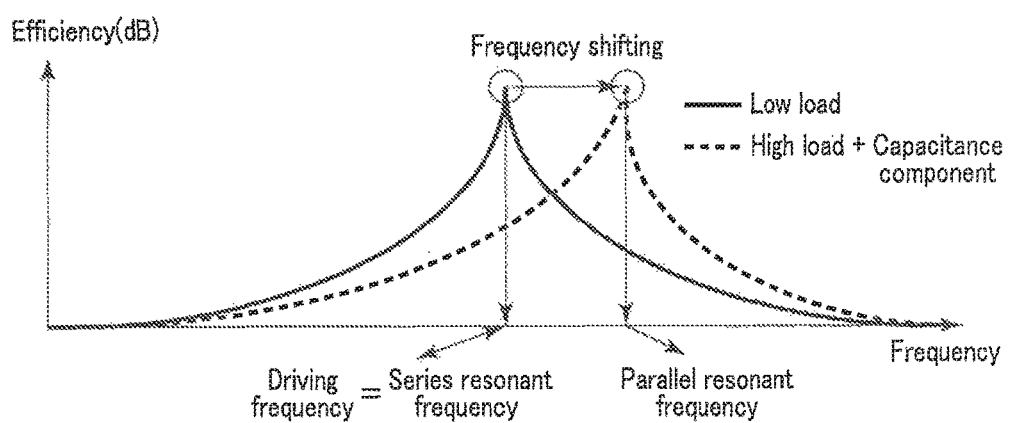
FIG. 3 is a view showing a comparison of efficiency between a living tissue of a low load and a living tissue of a high load.

FIG. 3 is a view showing a comparison of efficiency between a living tissue being a low load and a living tissue being a high load. In FIG. 3, the horizontal axis presents a frequency (driving frequency) of a high-frequency signal to be applied to a living tissue, whereas the vertical axis presents efficiency. In FIG. 3, the solid line presents efficiency when a living tissue is a low load, whereas the broken line presents efficiency when a living tissue is a high load.

During treatment, a living tissue as the load Z is generally given not only a resistance component but also a capacitance component due to an air bubble or degeneration of a cell membrane. That is, a living tissue becomes a capacitive load at the time of a high load. When a living tissue becomes a capacitive load, the resonant circuit including the parallel resonant circuit 106 and the series resonant circuit 110 is influenced by a capacitance component of the living tissue. This changes the filter characteristic of the resonant circuit when viewed as a filter circuit. Accordingly, as presented by the broken line in FIG. 3, a frequency (driving frequency) of a high-frequency signal to be applied to a living tissue shifts toward a higher frequency side at the time of a high load. Accompanying this shifting, a frequency (frequency corresponding to the peak of efficiency in FIG. 3) which makes driving most efficient also shifts toward a higher frequency side as compared to a frequency presented by the solid line in FIG. 3, which makes driving most efficient when a load is low.

In the resonant circuit, a deviation between the resonance frequency of the resonant circuit and a frequency which makes driving most efficient leads to decrease in efficiency. In addition, variation in a driving frequency causes variation in a waveform of a high-frequency signal to be applied to a living tissue. Such waveform variation destabilizes operation of the electric surgical instrument 200. The electric surgical instrument 200 such as an electric scalpel may be used to perform a control in which a state of a living tissue is monitored by measuring an impedance of an electrode in contact with the living tissue, and treatment of the living tissue is appropriately completed by stopping application of a high-frequency signal when the impedance reaches a predetermined state. Herein, if waveform variation is caused in a high-frequency signal to be applied to the electric surgical instrument 200, variation is also caused in the impedance to be measured. In such a case, it is difficult to monitor a state of a living tissue appropriately. When a state of a living tissue cannot be monitored appropriately, there is the possibility that a high-frequency signal is not sufficiently applied to complete treatment of a living tissue or is excessively applied so that the living tissue is adversely influenced. The electric surgical instrument 200, in particular, is used for a living tissue even in a high load state and therefore, has a tendency to cause such an influence of variation in a driving frequency.

Herein, in a low load state presented by the solid line in FIG. 3, the filter characteristic of the resonant circuit as a whole is more likely to be influenced by the series resonant circuit 110. In a high load state presented by the broken line in FIG. 3, the filter characteristic is more likely to be influenced by the parallel resonant circuit 106. Therefore, the efficiency can be improved by setting a parallel resonant frequency higher than a series resonant frequency. Preferably, the efficiency can be maximized by matching a series resonant frequency to a frequency which brings the best efficiency in a low load state and by matching a parallel resonant frequency to a frequency which brings the best efficiency in a high load state. It is desirable that how much a series resonance frequency is raised be set in accordance with the shifting amount of a frequency which brings the best efficiency when a living tissue is a high load. This shifting amount is obtained through simulations, etc.

As described above, according to the present embodiment, decrease in efficiency especially in a high load state can be improved by setting a parallel resonant frequency higher than a series resonant frequency in the power supply device 100 including the parallel resonant circuit and the series resonant circuit coupled to the parallel resonant circuit. In addition, frequency variation can also be suppressed in a driving signal when a load is high. This enables the electric surgical instrument 200 to operate stably during use.

[Modification 1]

Hereinafter, modifications of the present embodiment will be described. FIG. 4 is a view showing a configuration of a power supply device 100 according to the first modification of the present embodiment. In the power supply device 100 with the configuration shown in FIG. 2, the coil is shared by the parallel resonant circuit 106 and the transformer 108 which uses this coil as the primary winding. In the example shown in FIG. 4, on the other hand, a coil of a parallel resonant circuit 106 and a coil as a primary winding of a transformer 108 are separated from each other. That is, in FIG. 4, the coil as the primary winding of the transformer 108 is designated by L1, whereas the coil forming the parallel resonant circuit 106 is designated by L4 and this coil L4 is different from the coil L1. The configuration shown in FIG. 4 can also produce similar effects as those using the configuration shown in FIG. 2, by setting inductance values of coils L4 and L3 and capacitance values of condensers C1 and C2 in a manner that a parallel resonant frequency of the parallel resonant circuit 106 has a higher value than that of a series resonant frequency of a series resonant circuit 110.

[Modification 2]

FIG. 5 is a view showing a configuration of a power supply device 100 according to the second modification of the present embodiment. The power supply device 100 according to the second modification further includes a condenser C3 connected in parallel (that is, in parallel with respect to an electrode of an electric surgical instrument 200) between a series resonant circuit 110 and a living tissue as a load Z. A capacitance value of the condenser C3 is set smaller than that of a condenser C2 of the series resonant circuit 110. A capacitance value of the condenser C3 is, however, set greater than a value of a capacitance component of a living tissue as the load Z. In practice, a value of a capacitance component of a load is varied due to an influence of water vapor generated when a high-frequency signal is applied to a living tissue and a condition of the living tissue varied upon application of such a high-frequency signal. Accordingly, a capacitance value of the condenser C3 is set greater to some extent than a value predicted as a capacitance component of a living tissue.

An influence of a capacitance component of a living tissue can be made relatively small by forming the condenser C3. Addition of the condenser C3, however, decreases output impedance of the circuit. At this time, the efficiency decreases as the current shunt into the condenser C3 increases. Herein, setting a capacitance value of the condenser C3 smaller than that of the condenser C2 prevents the excessive current shunt into the condenser C3 and also the excessive decrease in efficiency. In addition, setting a capacitance value of the condenser C3 smaller than that of the condenser C2 reduces an influence of the condenser C3 on the series resonant circuit 110.

[Modification 3]

Figure 6:
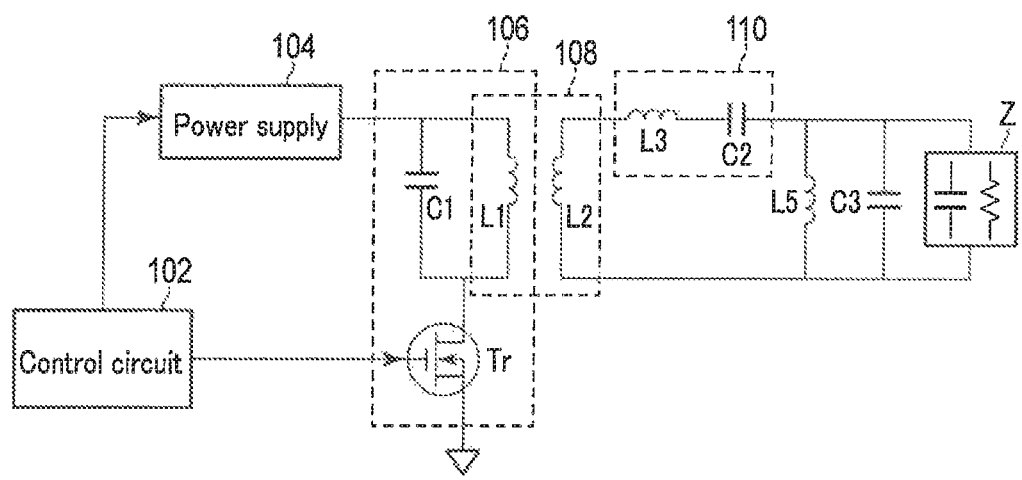
FIG. 6 is a view showing a configuration of a power supply device according to the third modification.

FIG. 6 is a view showing a configuration of a power supply device 100 according to the third modification of the present embodiment. The power supply device 100 according to the third modification further includes a filter circuit including a condenser C3 and a coil L5 connected in parallel (that is, in parallel with respect to an electrode of an electric surgical instrument 200) between a series resonant circuit 110 and a living tissue as a load Z.

As described in the second modification, addition of the condenser C3 results in the increased current shunt into the condenser C3. A high-frequency signal shunted into the condenser C3 is accumulated in the coil L5 and is then applied to a living tissue as the load Z. In this manner, decrease in efficiency due to addition of the condenser C3 can be further suppressed, and a capacitance value of the condenser C3 can be set larger than that of the condenser C2.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A high-frequency generator for an electric surgical instrument that treats a living tissue, the high-frequency generator comprising:

a power supply that generates a power;

a parallel resonant circuit that is connected to the power supply and that excites a high-frequency signal from the power generated at the power supply;

a transformer that transforms a voltage of the high-frequency signal excited at the parallel resonant circuit; and a series resonant circuit that is coupled to the parallel resonant circuit through both windings of the transformer and that is connected to the electric surgical instrument, wherein the parallel resonant circuit has a higher parallel resonant frequency than a series resonant frequency of the series resonant circuit.

2. The high-frequency generator according to claim 1, wherein the parallel resonant frequency is set based on an amount of variation in a frequency of the high-frequency signal caused by variation in a load of the living tissue with which the electrical surgical instrument is brought in contact.

3. The high-frequency generator according to claim 1,
wherein the parallel resonant circuit includes a first condenser and a first coil that are connected in parallel with respect to the power supply, and
wherein the first coil forms a primary winding of the transformer.

4. The high-frequency generator according to claim 1, wherein the series resonant circuit includes a second coil and a second condenser that are connected in series.

5. The high-frequency generator according to claim 4, further comprising a third condenser that is connected in parallel with respect to the electric surgical instrument, at an output terminal of the series resonant circuit, wherein the third condenser has a smaller capacitance than a capacitance of the second condenser.

6. The high-frequency generator according to claim 1, further comprising a fourth condenser and a third coil that are connected in parallel with respect to the electric surgical instrument, at an output terminal of the series resonant circuit.

7. The high-frequency generator according to claim 1, wherein the series resonant circuit is coupled to the parallel resonant circuit through a secondary winding of the transformer.

* * * * *